US007632440B2

United States Patent
Pickrell

(10) Patent No.: US 7,632,440 B2
(45) Date of Patent: Dec. 15, 2009

(54) POROUS CERAMIC, POLYMER AND METAL MATERIALS WITH PORES CREATED BY BIOLOGICAL FERMENTATION

(75) Inventor: Gary R. Pickrell, Blacksburg, VA (US)

(73) Assignee: Virginia Tech Intellectual Properties, Inc., Blacksburg, VA (US)

( * ) Notice: Subject to any disclaimer, the term of this patent is extended or adjusted under 35 U.S.C. 154(b) by 416 days.

(21) Appl. No.: 11/531,025

(22) Filed: Sep. 12, 2006

(65) Prior Publication Data

US 2007/0042456 A1 Feb. 22, 2007

Related U.S. Application Data

(62) Division of application No. 10/885,488, filed on Jul. 7, 2004, now Pat. No. 7,157,115.

(51) Int. Cl.
*B29C 44/22* (2006.01)
*C12N 1/16* (2006.01)
*C12N 1/32* (2006.01)

(52) U.S. Cl. .................. 264/42; 264/43; 435/255.1; 435/247

(58) Field of Classification Search ............. 264/42, 264/43; 435/255.1, 247
See application file for complete search history.

(56) References Cited

U.S. PATENT DOCUMENTS

| 4,383,823 A | 5/1983 | Williams et al. | 432/148 |
| 5,035,903 A | 7/1991 | Silva | 426/19 |
| 5,705,118 A * | 1/1998 | Hayes et al. | 264/656 |

* cited by examiner

*Primary Examiner*—Karen Cochrane Carlson
*Assistant Examiner*—Rosanne Kosson
(74) *Attorney, Agent, or Firm*—Whitham Curtis Christofferson & Cook, PC

(57) ABSTRACT

Porous polymers are made by adding biologically active agent and growth substrates (e.g., yeast and sugar, preferably in the presence of water or other suitable fluid) to a polymer forming material, which may be a liquid. The yeast acts on the sugar, forming carbon dioxide gas bubbles. The material is then polymerized so that the gas bubbles create permanent pores within the polymeric material. The polymer can be an epoxy for example. The pores will contain residue of the yeast. Also, porous metals can be made by combining a metal powder with yeast, sugar, and water. The porous metal paste is then sintered. Porous ceramics and semiconductors can be made by combining the yeast and sugar with a ceramic forming liquid such as polysilazane. Polysilazane converts to silica when heated, which helps to bind the ceramic or semiconductor powder particles at a reduced temperature. Biological agents other than yeast (e.g. bacteria, enzymes), and growth substrates other than sugar can also be used.

2 Claims, 1 Drawing Sheet

POROUS CERAMIC, POLYMER AND METAL MATERIALS WITH PORES CREATED BY BIOLOGICAL FERMENTATION

CROSS-REFERENCE TO RELATED APPLICATIONS

This application is a divisional of U.S. patent application Ser. No. 10/885,488 filed Jul. 7, 2004, now U.S. Pat. No. 7,157,115, and the complete contents thereof is herein incorporated by reference.

FIELD OF THE INVENTION

The present invention relates generally to methods for creating porous materials. More specifically, it relates to a method for creating pores in materials by biological fermentation (e.g. with bacteria or yeast or enzymes).

BACKGROUND OF THE INVENTION

Porous ceramic materials have been made previously by adding organic materials to the ceramic during fabrication, and then burning out the organic materials to leave holes or voids therein. For example, in brick manufacturing, sawdust or wood powder (i.e., "fugitive material") has been added to make the bricks lighter. On firing, the sawdust burns out, leaving a void where the wood once resided. This methodology has a number of drawbacks. In particular, it requires a significant amount of additional energy input (e.g., heating of the ceramic to combust the sawdust) and time. If the bricks are fired too fast, burning sawdust can cause the bricks to fracture. In addition, the burning process can leave a significant amount of residue to remove from the resulting porous ceramic material depending on the time and temperature of heating. Finally, the fugitive material adversely impacts profitability for the manufacturer by requiring space in the plant to store the material before use. This involves both an expense for storage and a decrease in the production capacity of the plant since some of the area is used up for storage purposes.

Porous polymeric materials can be made by a process wherein hollow glass spheres are combined with the polymer forming material. The density of the polymer composite can be varied by varying the density of the glass spheres and the volume fraction of spheres added. However, similar to prior porous ceramic structure manufacturing techniques, techniques for forming porous polymeric materials suffer from the fact that a very large volume of usable plant space must be reserved to store the large volumes of the glass spheres. This usage of space for storage of the glass spheres carries a very high cost both in overhead costs and in lost production capacity.

U.S. Pat. No. 5,071,747 to Hough et al. describes porous polymeric material, which in one embodiment, includes yeast within the pores of the material. The Hough invention contemplates formation of an emulsion from monomers and prepolymers, followed by polymerizing the monomers and prepolymers to yield a porous polymeric material, and finally, incorporation of the yeast within the pores. The yeast does not function to create the pores in the Hough device. Rather, the yeast provides biological activity in the device that is ultimately produced.

U.S. Pat. No. 4,603,111 to Keller describes a process for making a polyacrylamide bead, which in one embodiment incorporates yeast. The process involves combining the yeast with the acrylamide monomers, followed by polymerization. The resulting product is a bead with yeast immobilized thereon and therein. It was determined that the immobilized yeast retained the same activity of non-immobilized yeast. Thus, the beads could then be ideally used in later processes. It is noted that the yeast in Keller do not function in any capacity to form pores in the polyacrylamide bead.

U.S. Pat. No. 5,705,118 to Hayes describes a process for forming a ceramic material which includes combining an organic material such as gluten with a ceramic, followed by firing the ceramic material to form a green body. The gluten functions as a binder, and is ultimately eliminated by heat treatment in the manner discussed above in conjunction with prior technologies. Hayes indicates that minor amounts of yeast or enzymes, as well as many other constituents, may be included with the gluten, and that a "risen loaf" from the ceramic/gluten/yeast or enzyme mixture is ultimately fired.

U.S. Patent Publication 2003/0171822 to Lo describes a process for creating a porous synthetic bone graft wherein ceramic powder, binder and a pore-forming agent are combined in an inert liquid. The pore forming agent is then allowed to create the pores, and the porous structure is then fixed by a heat treatment. A high temperature heating is then used to eliminate the binder and the pore forming agent, and to fuse the structure together. Lo suggests that the pore forming agents could be yeast cells, alkali metal salts, and inorganic salts of acids derived from carbon and phosphorous. Lo indicates that a carbohydrate powder, and, in the case of yeast being used as the pore forming agent, sugar, are added to the slurry. Lo does not contemplate combining metal materials with the ceramic. Rather, in Lo, it is important to have pores in order to allow osteoblasts to attach in order to promote mineralization. Further, the Lo process methodology is not applicable to polymer materials as it requires the use of a binder, and a post pore forming, ceramic fusing heat step. Likewise, the Lo process suffers from the requirement of using carbohydrate powders and binders, which may result in porous structure where the pores are less uniform in size and/or are larger in size than is desired for certain industrial applications as opposed to applications in the human body.

It would be an advance in the art to provide a method for making porous materials that does not require large volumes of fugitive material. It would also be an advance to provide methods for making porous materials that can be used with metals, semiconductors, and polymers.

SUMMARY OF THE INVENTION

The present invention includes a porous polymeric material having closed pores, wherein the closed pores contain a biologic agent or a residue of biological agent. The residue can be a decomposition or desiccation product of yeast, bacteria or enzyme, for example. Carbon dioxide generated by the biological agent can also be trapped within the closed pores, but may also diffuse through the polymer material over time. The polymeric matrix material can be epoxy or a variety of other polymers or combinations of polymers.

The present invention also includes a method for making a porous polymeric material. In the method, a polymer forming material is mixed with a biological agent (e.g., yeast), and a growth substrate (e.g., sugar). The biological agent is allowed to act on the growth substrate and form gas bubbles. Then, the polymer forming material is polymerized, and in the process of polymerization, it traps gas bubbles therein. The size of the bubbles will vary depending on the polymer forming material used, rate of polymerization, and other processing conditions. The biological agent can act on the growth substrate at the same time that the polymer forming material is polymerizing.

The present invention also includes a method for making a porous ceramic or porous semiconductor material. In this method, a powder of ceramic or semiconductor material is mixed with a biological agent (e.g., yeast), a growth substrate (e.g., sugar), and a ceramic forming liquid binder (e.g., polysilazane). The biological agent is allowed to act on the growth substrate to form gas bubbles which separate powderized ceramic or semiconductor material except at particular points on the surfaces of the powder. The binder may hold the powderized ceramic or semiconductor material together at the points of contact. Then, the mixture is heated so that the ceramic forming liquid is converted to an oxide material, thereby binding the ceramic or semiconductor particles together. The material may be further heated to sinter the ceramic or semiconductor particles together.

The present invention also includes a method for making a porous metal material. In this method, a powder of metal material is mixed with a biological agent (e.g., yeast), and a growth substrate (e.g., sugar). The biological agent is allowed to act on the growth substrate to form gas bubbles. Then, the mixture is heated to bond the metal particles together. The metal particles, depending on the metal particles chosen, may also be sintered by further heat treatment.

The present invention also includes a porous ceramic with embedded metal wires. The ceramic can be made of many different ceramic materials, and the metal wires can be made of many different metal materials. The ceramic can be dried or baked at relatively low temperature, or may be sintered at relatively high temperature.

DESCRIPTION OF THE DRAWING FIGURES

DETAILED DESCRIPTION OF THE PREFERRED EMBODIMENTS OF THE INVENTION

Figure 1:
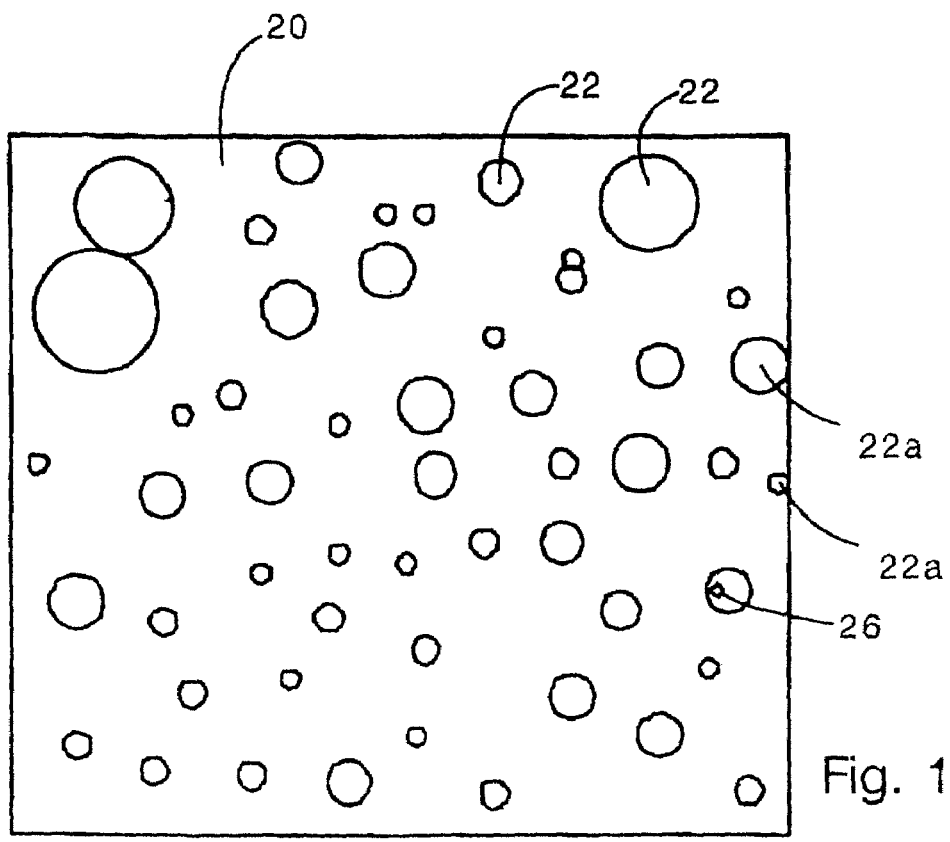
FIG. 1 shows a porous polymer material made according to the present invention.

The present invention provides several methods for making porous polymers, metals, semiconductors and ceramics.

For making porous polymers according to the present invention, polymer forming material (e.g., monomers or oligomers) or an already formed polymer is mixed with a combination of biologically active material (preferably yeast, but also may include bacteria or enzymes), a growth substrate (preferably sugar, but also may include polysaccharides, mixtures of sugars, and other materials which can be acted upon by the biologically active material to produce a gaseous byproduct), and preferably a fluid carrier (e.g., preferably water, but any fluid which allows mixing of the polymer forming material or polymer, biologically active material and growth substrate, and which does not inhibit the activity of the biologically active material would be acceptable). In the most preferred embodiment, yeast, sugar and water are used in combination with a polymer forming material. In this embodiment, the yeast is allowed to ferment the sugar to produce carbon dioxide bubbles in the polymer as the polymer forming material is polymerized. Polymerization can proceed by a variety of different mechanisms including without limitation condensation or step-type polymerizations, free-radical polymerizations, ionic and coordination polymerization, ring opening polymerization, and photolytic or electrolytic polymerization. Polymerization can be initiated by a variety of different mechanisms including addition of a catalyst, addition of one or more reactants, application of radiant energy (e.g., UV radiation), and application of heat. The polymer formed can be aqueous (i.e. water-soluble) or non-aqueous (immiscible in water).

In some embodiments of this invention, such as where the polymer is water soluble, or under conditions where the polymer is of a consistency that allows water droplets carrying the biologically active material and the substrate to be dispersed therein, a preformed polymer can be used.

In another aspect, a ceramic or semiconductor powder (e.g., silicon) is combined with a ceramic forming liquid binder (e.g., polysilazane, alumoxane, etc.), and a combination of biologically active agent, a growth substrate, and preferably a fluid (e.g., yeast, sugar and water, respectively). After the yeast ferments and produces gas bubbles in the mixture, the material is heated to sinter the ceramic or semiconductor to form a porous material. The ceramic forming binder converts to an oxide, carbide or nitride during the sintering step (e.g. polysilazane converts to nitride or silica depending on temperature).

In another aspect, a ceramic powder is combined with metal wires, and a combination of biologically active agent, a growth substrate, and preferably a fluid (e.g., yeast, sugar and water, respectively). An optional binder, such as wheat gluten, wheat flour or polysilazane may also be added. After sintering, the metal wires remain in the porous material and provide unusual and useful properties heretofore not available.

In another aspect, a metal powder (e.g. stainless steel, copper, bronze, zirconia) is combined with a mixture of a biologically active agent, a growth substrate, and preferably a fluid (e.g., yeast, sugar and water, respectively). The yeast produces pores in the material, and the metal powder is then sintered, resulting in a porous metal material.

Porous Polymer Materials

Porous polymeric materials are preferably made in the present invention by mixing a polymer-forming material (e.g. monomers, oligomers, and reactants and/or catalysts) or an already formed polymer together with a combination of yeast, sugar and water (and optionally salt and other nutrients). After mixing, the mixture is left to stand so that the yeast consumes the sugar and produces carbon dioxide. The carbon dioxide forms gas bubbles that remain trapped within the polymer formed from the polymer forming material. The polymer forming material may be polymerized before, during or after the yeast causes carbon dioxide bubbles to be produced. The polymer material may trap the carbon dioxide bubbles thus formed within the porous material. However, depending on the nature of the polymer employed, the carbon dioxide may either leach out of the porous material over a period of time, or be trapped within the polymer in gas pockets for an extended period of time.

The polymer or polymer forming material can vary widely within the practice of the invention and will depend on the needs of the application. For example, the polymer forming material can be a 2-part epoxy, 1-part epoxy, polyester resin, silicone, phenolic, rubber or any other polymerizable material. The polymer can be a hard polymer (e.g., phenolic or epoxy), or a soft elastomer (e.g., rubber or silicone). The polymer forming material will typically be a liquid until it is polymerized. In applications involving an aqueous polymer, the polymeric material will be present in the mixture in already polymerized form, and the gas formation caused by the yeast and sugar will take place as the water is evaporated from a mixture containing the aqueous polymer.

The relative proportions of polymer forming material, yeast, sugar and water can vary widely. The relative proportions can be selected to produce a desired porosity or pore connectivity (e.g., connected pores or non-connected pores (i.e., singular, un-connected voids within the polymeric material)). For example, the polymer forming material can comprise about 40-80% by volume, with the sugar and water each comprising about 5-20% by volume, and the yeast comprising 1-10% by volume. These ranges are exemplary only and are not limiting to the appended claims.

In order to provide uniform pore distribution, the mixture can be continuously mixed while the yeast acts upon the sugar. Mixing can continue until the mixture reaches a predetermined viscosity. For example, mixing can be halted when the viscosity is high enough to assure that the bubbles will not rise and separate from the polymeric material. Mixing until high viscosity is achieved will tend to reduce the size of the bubbles and possibly elongate the bubbles into long tubes which may be desirable in some applications.

Preferably, the mixture has a sufficiently high viscosity to prevent gas bubbles from rising without continuous mixing. Optionally, in order to provide a high enough viscosity the material can be partially polymerized before or during gas generation (e.g., yeast or bacterial fermentation, or enzymatic reaction). Partial polymerization tends to increase the viscosity and inhibit separation of the bubbles from the polymer.

Many different biologically active agents other than yeast can be used. For example, bacteria or viruses can be used. The biological agent must form a gas as it consumes and/or interacts with the growth substrate (e.g., sugar) in the mixture.

The biological agent may need to be selected for compatibility with the polymeric material. For example, some polymer-forming materials might be toxic to certain bacteria or yeasts. It is essential in the invention that the biological agent remains metabolically active while exposed to the polymer-forming material.

Many growth substrates other than sugar can be used. For example, carbohydrates, fats, proteins, mixtures thereof or other substrate materials (e.g., wheat flour) can be provided in the mixture. Whatever growth substrate is provided, the biological agent must be able to consume and/or interact with it and produce bubble-forming gases. Nutrients such as salt, minerals or B-vitamins can also be added to enhance the generation of bubbles or to provide improved environmental conditions for the biological agent.

The polymer forming material can be water-soluble (e.g., (PAM) polyacrylamide, methylcellulose, or (PVA) polyvinyl alcohol) or water-immiscible (e.g., epoxy, polyester resin, polyamides, or polyimides). If the polymer forming material is water soluble, then the yeast, sugar and water will be wetted and uniformly distributed within the material after mixing. If the polymer forming material is water-immiscible, then the yeast, sugar and water will form tiny droplets within the polymer-forming material. In either case, mixing might be desirable to encourage the uniform distribution of gas bubbles.

The polymer forming material can be polymerized by any known method. The polymer forming material can be polymerized in the presence of heat or radiant energy, or by the addition of a chemical catalyst, for example. If a chemical catalyst is used, it can be incorporated into the mixture before or after the gas bubbles are formed. In some applications, the polymerizing step can inactivate or kill the biological agent (e.g., UV exposure is known to kill a variety of organisms; heat also can kill a variety of organisms; further the choice of polymeric material may result in surface interactions that kill the biological agent).

The porosity of the porous polymer produced can be controlled and adjusted by a number of mechanisms. For example, the porosity might be controlled by controlling the duration or temperature of the fermentation, or by adjusting the quantity or composition of the growth substrate. The present porous polymer material can have a wide range of porosities, for example up to 50 or 75%. Typically, some of the pores in the material will be open pores (i.e., open to the external environment) and some will be closed pores (i.e., isolated from the external environment).

The present method for making porous polymeric materials is suitable for making molded parts or other shaped items. After mixing the materials, and before or after the formation of bubbles, the bubbly mixture can be poured into a mold, extruded through a die, or otherwise shaped.

The porous polymers made according to the present invention will necessarily have either the biological agent itself or a residue of the biological agent trapped within the closed pores. The open pores may or may not contain similar agent or residue. The residue may comprise dead, dried or decomposed yeast, bacteria, or inactive or active enzymes used in combination with the growth substrate to generate the gas bubbles. The closed pores may also contain a portion of unconsumed growth substrate or nutrient materials.

The closed pores might also contain water. The water might be left over from the original mixture (e.g., from the yeast, sugar and water mixture), or might be created by polymerization. Also, it is possible in some polymer materials for the water to slowly diffuse through the polymer and open pores, so that the closed pores contain only dried biological agent and growth substrate residue.

FIG. 1 shows a porous polymeric material according to the present invention. The porous material comprises a solid polymeric matrix 20. Gas-filled and/or empty pores 22 are disposed within the polymeric matrix. The pores 22 typically will have many different sizes, for example in the range of 0.1 micron to several millimeters. The pore size will typically depend on the processing (e.g., mixing or agitation) of the polymeric material during polymerization or on the reaction conditions and the amounts of biologically active agent and growth substrate provided. Although the pores are shown as spherical, the pores can be any shape.

The pores 22 can be open or closed to the outside environment. Typically, some pores will be open, and some pores will be closed. Pores 22a are open to the outside environment. In the present invention, the closed pores (i.e., pores with trapped contents) will contain the biological agent or a residue of biological agent 26. The residue 26 can comprise any decomposition or desiccated product of a biological active agent (e.g., bacteria, yeast, enzyme).

The present porous polymer material is well suited for use in applications where lightweight polymer materials are needed. Also, the present porous polymer tends to reduce the amount of polymer material needed to fabricate a part with a given volume, which can reduce the component cost.

EXAMPLE 1

In this experiment, the biological agent was commercially available baking yeast. The polymer system chosen for demonstration was a common two-part epoxy—Epoxy 907, commercially available from Miller-Stephenson. Equal parts of the two-part epoxy were used. In one example, approximately 15 grams of each epoxy part was used, along with approximately 2 grams of yeast, 5 grams of sugar and 5 grams of water. The yeast, water, sugar, and epoxy were mixed together in a beaker. In some cases 1 gram of salt was used as well, and the yeast, sugar, water, and salt were mixed in a beaker first and the yeast mixture was allowed to stand for a few minutes. This mixture was then added to the epoxy and mixed. After mixing for a short period of time, the epoxy was allowed to rise in a mold. The article was then observed by optical microscopy, and the densities characterized by Archimedes method. Pore sizes were in the range of approximately a few millimeters to tens of microns. Porosity was up to about 50% by volume.

Samples of the porous epoxy material were exposed to water and the water was not absorbed. This was most likely due to the surface tension of the water in contact with the polymer and the hydrophobic nature of the epoxy. It was possible that the pores, which existed in the specimen, were "closed", such that the fluid could not be absorbed into the pores just below the surface of the specimen. To test, alcohol was placed on the sample, which was quickly absorbed. This indicated a significant amount of open porosity was present in the sample. To determine the amount of total porosity, percent open porosity and percent closed porosity, a modification of Archimedes method was used with alcohol as the fluid medium.

A sample was cut into a parallelogram, weighed dry, placed in alcohol to saturate, weighed saturated, and weighed suspended. Based on these weights, the sample was calculated to contain approximately 30% by volume open porosity, 20% by volume closed porosity (i.e., 50% total porosity). The pores, which varied in size from a few mm to the micron range or below, was random in both size and spatial distribution.

Porous Metal Method

The present invention includes a method for making porous metals and metal foams in which a metal powder is mixed with a combination of biological active agent (e.g., yeast), a growth substrate (e.g., sugar), and fluid (e.g., water). As above, the biological active agent can be any of yeast, bacteria or enzyme that consumes or interacts with the growth substrate so as to produce gas bubbles. The substrate can be, for example, any sugar, carbohydrate, fat, protein or mixture thereof.

In a manner similar to producing porous polymers, the porous metal material is made by mixing the metal powder with, for example, the yeast, sugar and water to form a slurry or paste. The yeast, or other biologically active agent, is then allowed to act on the growth substrate to produce, for example, carbon dioxide gas in the case of sugar and/or other polysaccharide materials being used as the growth substrate. As the yeast produces gas, bubbles are formed in the mixture. After bubbles are formed, the mixture is heated to bond or sinter the metal powder particles. The yeast and sugar might or might not be burned out during the heating step; some yeast or sugar may remain in the final product.

The metal powder can be made of many different metals or metals alloys. For example, the metal powder can be made of aluminum, copper, stainless steel, brass, bronze, or other metals.

Optionally, a binding agent is also provided. The binding agent functions to hold the metal powder together as it is heated to sintering temperature. The binding agent can be an ceramic forming liquid (e.g., polysilazane, alumoxane, etc.), methylcellulose, acrylic, soluble or insoluble fiber or other polysaccharide gums, or wheat flour or gluten. Alternatively, the binding agent can be a low-melting point metal (e.g., tin, lead, bismuth, or zinc) that may hold the metal powder together by surface tension. The low melting point metal can be provided in the form of a powder.

In some applications, it may be necessary to perform the heating or sintering step in an oxygen-free or reducing atmosphere (e.g., in nitrogen, hydrogen, or argon).

In another aspect of the invention, the porous metal material includes metal wires. The wires can have a small diameter (e.g. tens or hundreds of microns). The wires can have short lengths of several millimeters or several centimeters. The wires tend to strengthen the porous metal material by distributing tensile and compressive forces. The wires can be made of stainless steel, for example.

Additionally, the porous metal material can include a portion of a ceramic powder.

Porous Ceramic or Semiconductor Method

The present invention also includes porous ceramic or semiconductor material made with a ceramic forming liquid binder such as polysilazane, alumoxane, or silicate. In this aspect of the invention, the porous structure is formed by a biological active agent acting on a growth substrate, as described above. The biological active agent can be any yeast, bacteria or enzyme that consumes or interacts with the substrate to produce gas bubbles. The substrate can be any sugar, carbohydrate, fat, protein or mixture thereof.

Polysilazane and alumoxane convert to oxide, carbide or nitride ceramic materials when heated. Silicates that form silica can also be used as the ceramic forming material. The ceramic material formed from the binder liquid tends to assist in bonding the ceramic or semiconductor particles together. Therefore, the ceramic forming liquid binder can reduce the temperature required for hardening or sintering the material. This can be a great advantage because sintering at high temperature can be very energy consumptive and expensive. By reducing the temperature required for bonding, and/or reducing the high temperature firing duration, the ceramic forming liquid can greatly reduce the time and cost required to make porous ceramics and porous semiconductor materials.

In the case of ceramic, the ceramic powder can comprise many different ceramics such as zirconia, alumina, silica, silicon nitride silicon aluminum oxynitride, silicon carbide, clay, porcelain, mullite, codierite, and the like.

In the case of semiconductor, the semiconductor can comprise many different semiconductor materials including silicon, germanium and the like. Also, compound semiconductors can be used (e.g., 3-5 or 2-6 materials). The use of ceramic forming liquids for producing porous compound semiconductors can be advantageous in the case of compound semiconductors because some compound semiconductors cannot withstand high temperatures required for sintering.

Also, it is noted that the present invention contemplates a porous material comprising mixtures of ceramics and semiconductors, with the particles adhered by the decomposition product of the ceramic forming liquid binder.

Additionally, it is noted that many different kinds of ceramic forming liquids can be used. Additionally, it is noted that the ceramic forming liquid can be diluted with a solvent to control the amount of oxide material formed during baking.

Semiconductor Powder Example

Silicon Powder (ground with a mortar and pestle to a fine consistency)—1 gram;

Polysilazane (binder)—1 gram

Yeast 5 grams

Water 15 grams

Sugar 10 grams

The yeast, sugar and water were added to a separate beaker and mixed. This mixture was set aside to allow the yeast to activate. The silicon metal powder was mixed with the polysilazane thoroughly. The yeast and silicon mixtures were then combined. The resulting mixture was formed into two small pellets and heated gently with a heat gun to set the binder.

Porous Ceramic with Metal Wires

The present invention also includes a porous ceramic material comprising embedded metal wires. Preferably, the porous ceramic is made by a biological active agent acting on a growth substrate, as described above.

Figure 2:
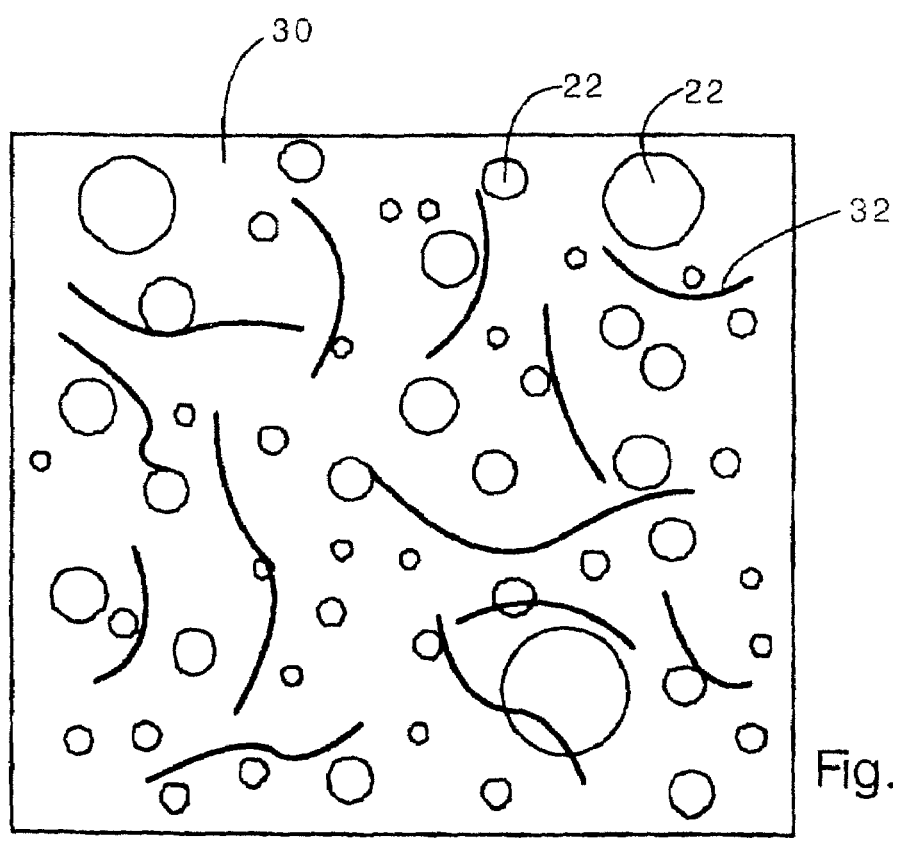
FIG. 2 shows a porous ceramic with metal wires according to the present invention.

FIG. 2 shows a ceramic 30 with embedded metal wires 32 according to the present invention. The ceramic is porous and has pores 22. The wires 32 can have diameters of tens or hundreds of microns and lengths of several millimeters or several centimeters. The wires can be made of stainless steel, copper, aluminum brass, bronze, titanium, tungsten, nickel or other metals for example. The wires can comprise less than 1% or more than 5%, 10% or 20% of the composite material volume, for example.

The ceramic powder can comprise many different ceramics such as zirconia, alumina, silica, silicon nitride, silicon aluminum oxynitride, silicon carbide, clay, porcelain, mullite, codierite, and the like.

The embodiment with metal wires can be made by adding chopped metal wires to a mixture of ceramic powder, yeast (or other biological agent), sugar (or other growth substrate) and water (or other fluid). After the fermentation step, the material is dried, baked or sintered. Sintering or heating is not necessarily required for creating a hard and durable material. If the material is sintered at high temperature, it is preferable for the sintering temperature of the ceramic to be less than the melting temperature of the metal wire. The particle size of the ceramic material may be selected to be small so that the ceramic material sinters at a temperature lower than the wire melting temperature.

Porous composites comprised of metallic wires and ceramic lattice may have many potential uses. Reducing the density of a ceramic material, in general, reduces the strength and toughness of the material, as is well know in the field. In some cases, very low-density materials can be made (for example, 95% by volume air), but in general, these low-density materials are difficult to handle because they are brittle and are of low strength and toughness. Addition of metal wires will improve the strength and toughness of these materials. For example, porous thermal insulation materials, filtration media, etc., may be envisioned with increased strength and toughness. This might benefit a wide array of applications, including tiles for space shuttles, refractory furnace insulation, filtration media (air, water and molten metal), etc.

Also, the wires 32 can provide electrical conductivity to the porous ceramic, and can absorb or block electromagnetic radiation or certain frequencies of electromagnetic radiation. Also, the wires can improve the thermal shock resistance of the part, which may be very beneficial in applications such as kiln furniture or insulating tiles. In this application, the wires are preferably made of a metal with a high thermal conductivity (e.g. copper).

Metallic materials of various types, such as platinum, rhodium, etc, are often used in catalytic applications. Many of these materials are very expensive which prohibits manufacturing and use of monolithic pieces in the catalytic applications. Instead, ceramic supports are often used as "substrates" to hold the film or coating of the precious metal material. Utilizing a porous composite material which incorporates metallic wires, may allow improve catalytic efficiency per unit weight of the catalytic material used. The substrates, which are coated with the precious metal, only allow interaction of the material to be reacted with the top surface of the catalyst. The bottom surface of the catalyst is in contact with only the substrate and not the reacting gases. Essentially, the bottom surface is wasted as far as the catalytic reactions are concerned. However, utilizing a highly porous ceramic substrate into which the "wires" of the catalytic material are incorporated may allow reaction of the material around the entire circumference of the metal wire. The critical parameters, which can be varied to tune the catalytic activity, include the amount of porosity produced, the size range distribution of the porosity, the diameters of the wires used and the length of the wires. Also, tailoring the parameters of forming, such as the "wetability" of the metal wires by the ceramic phase, can dictate where the wires occur in the composite. Also, tailoring the surface properties of the metal wires (for example by coatings), can dictate where the yeast cells multiply and where they will be killed. For example, if the sugar necessary for the yeast cells to multiply is coated onto the wires before addition to the mixture, it may be possible to preferentially grow the yeast cells around the wires. Likewise, a fungicide applied to the wires may be able to retard growth of the yeast cells in the vicinity of the wires. Upon heating, the fungicidal material could be removed if desired. In some applications, however, it may be advantageous to leave the fungicidal, germicidal or disinfecting agent within the porous material, which may produce parts that do not allow growth of these agents. Many schemes may be envisioned to tailor how the porosity forms in relation to the wires and this may dictate the control of the degree of surface area of the fibers available for the catalytic reactions.

The function of the ceramic material is to provide the substrate for holding the fine diameter wires. Many catalytic operations are performed at high temperatures and in relatively corrosive environments where the ceramic materials can provide both refractoriness and inertness. The metallic wires serve as the catalytic sites. The yeast, which produces the porosity, serves to open the interior of the part to the catalytic reactions and allow the gases and/or liquids to permeate into the interior of the part through the large amount of open porosity present. Therefore, the entire volume of the porous part is available for the catalytic reactions. Also, incorporating the wires into the composite will eliminate the need to coat the substrate with the precious metal (which is a common current method) after formation of the substrate. The coating process is costly, time consuming and in many cases is difficult to control to ensure uniform coating thickness throughout the parts. Utilizing metal wires may eliminate these problems, by incorporating the catalytic material directly into the part during fabrication, and by using controlled diameter wires.

Metal Powder/Ceramic Powder Composite Example

Ingredients: Stainless Steel chopped wires 1.5 gram
  Zirconia Powder 2.0 gram
  Duramax binder 1.2 gram
  Water 0.1 gram
  Sugar 0.4 gram
  Yeast 0.2 gram The ingredients were mixed together and formed into two balls and a small flat disk. The samples were allowed to dry for several days after which a porous metal, ceramic, polymer composites was formed.

It will be clear to one skilled in the art that the above embodiment may be altered in many ways without departing from the scope of the invention. Accordingly, the scope of the invention should be determined by the following claims and their legal equivalents.

What is claimed is:

1. A method for making a porous ceramic or semiconductor material, comprising the steps of:
   a) mixing the following:
      a ceramic or semiconductor powder,
      a microorganism or enzyme that can ferment a sugar,
      a sugar, and
      a ceramic forming binder liquid selected from the group consisting of: polysilazanes, alumoxanes, and silicates, to form a mixture;
   b) allowing the microorganism or enzyme to act on the sugar so as to produce gas bubbles in the mixture; and
   c) heating the mixture so that the ceramic forming binder liquid is converted to a ceramic material.

2. The method of claim 1 wherein the ceramic material is selected from the group consisting of: oxides, carbides, and nitrides.

* * * * *